US006645547B1

(12) United States Patent
Shekalim et al.

(10) Patent No.: US 6,645,547 B1
(45) Date of Patent: Nov. 11, 2003

(54) STENT COATING DEVICE

(75) Inventors: Avraham Shekalim, Nesher (IL); Ascher Shmulewitz, Tel Aviv (IL)

(73) Assignee: Labcoat Ltd., Galway (IE)

( * ) Notice: Subject to any disclaimer, the term of this patent is extended or adjusted under 35 U.S.C. 154(b) by 0 days.

(21) Appl. No.: 10/136,295

(22) Filed: May 2, 2002

(51) Int. Cl.[7] .......................... B05D 1/26; A61L 27/00; A61L 27/54

(52) U.S. Cl. ..................... 427/2.24; 427/2.1; 427/2.25; 427/2.28; 427/2.3; 427/258; 427/261; 427/287; 427/424; 427/425; 118/668; 118/669; 118/679; 118/680

(58) Field of Search ................................ 427/2.1, 2.24, 427/2.25, 2.28, 2.3, 258, 261, 287, 424, 425; 118/668, 669, 679, 680

(56) References Cited

U.S. PATENT DOCUMENTS

| | | | |
|---|---|---|---|
| 5,755,781 A | | 5/1998 | Jayaraman |
| 5,871,436 A | | 2/1999 | Eury |
| 5,891,507 A | | 4/1999 | Jayaraman |
| 5,922,393 A | | 7/1999 | Jayaraman |
| 5,972,027 A | | 10/1999 | Johnson |
| 6,001,311 A | | 12/1999 | Brennan |
| 6,042,600 A | | 3/2000 | Rosenthal et al. |
| 6,106,454 A | | 8/2000 | Berg et al. |
| 6,129,658 A | | 10/2000 | Delfino et al. |
| 6,171,232 B1 | | 1/2001 | Papandreou et al. |
| 6,203,551 B1 | | 3/2001 | Wu |
| 6,214,115 B1 | | 4/2001 | Taylor et al. |
| 6,235,340 B1 | | 5/2001 | Lee et al. |
| 6,245,104 B1 | | 6/2001 | Alt |
| 6,309,380 B1 | | 10/2001 | Larson et al. |
| 6,335,029 B1 | | 1/2002 | Kamath et al. |
| 6,368,658 B1 | | 4/2002 | Schwarz et al. |
| 6,395,326 B1 | * | 5/2002 | Castro et al. .............. 427/2.24 |

FOREIGN PATENT DOCUMENTS

WO WO02/14078 2/2002

OTHER PUBLICATIONS

"Applications of Ink–Jet Printing Technology to BioMems and Microfluidic Systems" Cooley et al; Proceedings, SPIE Conference on Microfluidics and BioMems Oct. 2001.

* cited by examiner

*Primary Examiner*—Shrive P. Beck
*Assistant Examiner*—Jennifer Kolb Michener
(74) *Attorney, Agent, or Firm*—Finnegan, Henderson, Farabow, Garrett & Dunner LLP

(57) ABSTRACT

The present invention is a method and device, which is suitable for use in an operating theater just prior to implantation, for selectively applying a medical coating to an implantable medical device, for example a stent. Disclosed is a device for use with a stent deployed on a catheter balloon. The device is configured to apply a medical coating of a desired thickness to the surface of a stent only. This is done by use of a drop-on-demand ink-jet printing system in association with an optical scanning device. The device is further configured so as to, if necessary, apply a plurality of layered coats, each layered coat being of a different coating material, and if appropriate, different thickness. The section of the housing in which the stent is held during the coating procedure is detachable from the housing base. The detachable housing section may be easily cleaned and re-sterilized or simply disposed of.

15 Claims, 6 Drawing Sheets

STENT COATING DEVICE

FIELD AND BACKGROUND OF THE INVENTION

The present invention relates to the coating of medical devices intended for in vivo deployment and, in particular, it concerns a method and device, which is suitable for use in an operating theater just prior to implantation, for selectively applying a medical coating to an implantable medical device, for example a stent.

The practice of coating implantable medical devices with a synthetic or biological active or inactive agent is known. Numerous processes have been proposed for the application of such a coating. Soaking or dipping the implantable device in a bath of liquid medication is suggested by U.S. Pat. No. 5,922,393 to Jayaraman, soaking in an agitated bath, U.S Pat. No. 6,129,658 to Delfino et al. Devices introducing heat and/or ultrasonic energy in conjunction with the medicated bath are disclosed in U.S. Pat. No. 5,891,507 to Jayaraman and U.S. Pat. No. 6,245,104 B1 to Alt. The device of U.S. Pat. No. 6,214,115 B1 to Taylor et al. suggest spraying the medication by way of pressurized nozzles.

Initially such coating were applied at the time of manufacture. For various reasons such as the short shelf life of some drugs combined with the time span from manufacture to implantation and the possible decision of the medical staff involved concerning the specific drug and dosage to be used based on the patient's at the time of implantation, have lead to methods and devices for applying a coating just prior to implantation. Wrapping the implantable device with medicated conformal film is disclosed in U.S. Pat. No. 6,309,380 B1 to Larson et al. Dipping or soaking in a medicated bath just prior to implantation are suggested in U.S. Pat. No. 5,871,436 to Eury, U.S. Pat. No. 6,106,454 to Berg et al., and U.S. Pat. No. 6,1171,232 B1 to Papandreou et al. U.S. Pat. No. 6,203,551 B1 to Wu provides a bathing chamber for use with specific implantable device such as the stent deployed on the balloon of a catheter (FIG. 1).

Each of the methods and devices intended for use just prior to implantation, listed above, deposit the coating material onto any and all surfaces that are exposed to the coating. This may result in depositing coating material on surfaces on which the coating is unwanted or undesirable. Further, the coating may crack or break away when the implantable is removed from the implantation apparatus. An example of this would be a stent deployed on a catheter balloon. As the balloon is inflated and the stent is expanded into position, the coating may crack along the interface between the stent and the balloon. These cracks may lead to a breaking away of a portion of the coating from the stent itself. This, in turn, may affect the medicinal effectiveness of the coating, and negatively affect the entire medical procedure.

It is further know to use Ink-Jet technology to apply a liquid to selected portion of a surface. In the paper "Applications of Ink-Jet Printing Technology to BioMEMS and Microfluidic Systems," presented at the SPIC Conference on Microfluidics and BioMEMS, October, 2001, the authors, Patrick Cooley, David Wallace, and Bogdan Antohe provide a fairly detailed description of Ink-Jet technology and the range of its medically related applications (http://www.microfab.com/papers/papers_pdf/spie_biomems_01_reprint.pdf). A related device is disclosed in U.S. Pat. No. 6,001,311 to Brennan, which uses a moveable two-dimensional array of nozzles to deposit a plurality of different liquid reagents into receiving chambers. In the presentation of Cooley and the device of Brennan, the selective application of the material is based on an objective predetermined location of deposit rather that on a subjective placement as needed to meet the requirements of a specific application procedure. With regard to the application of coatings applied to medical devices with ink-jet applicators, while it is possible to coat only a chosen portion of a device, such as only the stent mounted of a catheter, but not the catheter itself. This type of procedure using current device may, however, require providing complex data files, such as a CAD image of the device to be coated, and insuring that the device be installed in the coating apparatus in a precise manner so as to be oriented exactly the same as the CAD image.

There is therefore a need for a device, and method for its use, whereby.a coating is selectively applied to an implantable medical device just prior to implantation, such that only the device or selected portions thereof are coated. It would be desirable for the device to provide for user selection of coating material and dosage to be applied, thereby providing choices as to the specific coating material and dosage to be applied based on the specific needs of the patient at the time of implantation. It would be further desirable for the device to provide a sterile environment in which the coating is applied and the device is suitable for use in an operating theater.

SUMMARY OF THE INVENTION

The present invention is a method and device, which is suitable for use in an operating theater just prior to implantation, for selectively applying a medical coating to an implantable medical device, for example a stent.

According to the teachings of the present invention there is provided, a coating device for selectively applying a coating to surfaces of an object, the device applying the coating based upon optical properties of the surfaces such that the coating is applied to surfaces of a first type and is not applied to surfaces of a second type, the first type of surface being optically distinguishable from the second type of surface, the coating device comprising: at least one object-holding element configured to hold the object while a coating is applied; at least one optical scanning device deployed so as to scan at least a portion of the object, the optical scanning device configured so as to produce output indicative of the types of surfaces of the object; at least one coating applicator deployed so as to deposit a fluid so as to coat at least a portion of the object; at least one fluid delivery system in fluid communication so as to supply the fluid to the coating applicator; a processing unit being responsive at least to the output so as to selectively activate the coating applicator, thereby applying the coating substantially only to surfaces of the first type; and a drive system configured so as to provide relative motion between the surface of the object and the coating applicator, and between the surface of the object and the optical scanning device.

According to a further teaching of the present invention, the drive system is configured so as to rotate the object-holding element about an axis perpendicular to a direction of application of the coating applicator.

According to a further teaching of the present invention, the at least one object-holding element is implemented as two object-holding elements configured so as to simultaneously support the object at two different regions along a length of the object.

According to a further teaching of the present invention, the two object-holding elements are mechanically linked so as to rotate synchronously about a single axis, the axis being perpendicular to a direction of application of the coating applicator.

According to a further teaching of the present invention, the at least one coating applicator includes a pressure-pulse actuated drop-ejection system with at least one nozzle.

According to a further teaching of the present invention, a spatial relationship between the coating applicator and the object is variable.

According to a further teaching of the present invention, the spatial relationship is varied along a first axis that is parallel to a direction of application of the coating applicator, and a second axis that is perpendicular to the direction of application of the coating applicator.

According to a further teaching of the present invention, the coating applicator is displaceable relative to the object-holding element, the displacement being along the first axis and the second axis, thereby varying the spatial relationship.

According to a further teaching of the present invention, both the coating applicator and the optical scanning device are deployed on a displaceable applicator base, displaceable relative to the object-holding element, the displacement being along the first axis and the second axis, thereby varying the spatial relationship.

According to a further teaching of the present invention, the at least one coating applicator is implemented as a plurality of coating applicators and the at least one fluid delivery system is implemented as an equal number of fluid delivery systems, each fluid delivery system supplying a different fluid coating material to the coating applicator with which the each fluid delivery system is in fluid communication.

According to a further teaching of the present invention, the object is a catheter that includes a balloon portion on which a stent is deployed, such that the stent is a surface of the first type and the balloon is a surface of the second type surface.

According to a further teaching of the present invention, the processing unit is responsive to an indication of the relative motion so as to change operational parameters of the coating device as required.

According to a further teaching of the present invention, the object-holding element, the coating applicator, the optical scanning device, the drive system and at least a portion of the fluid delivery system are deployed within a housing that includes an application compartment.

According to a further teaching of the present invention, the housing includes a base housing section and a detachable housing section.

According to a further teaching of the present invention, the application compartment is defined by portions of both the base housing section and the detachable housing section.

According to a further teaching of the present invention, the base housing section includes the coating applicator, at least a portion of the fluid delivery system, the optical scanning device and the processing unit and at least a first portion of the drive system, and the detachable housing section includes the object-holding element and at least a second portion of the drive system.

According to a further teaching of the present invention, the base housing section includes at least one fluid delivery system.

According to a further teaching of the present invention, the detachable housing section is disposable.

According to a further teaching of the present invention, the application compartment is a substantially sterile environment.

According to a further teaching of the present invention, the coating applicator, and the fluid delivery system are included in a removable sub-housing, the removable sub-housing being deployed with in the application compartment and the removable housing being detachably connected to the processing unit.

There is also provided according to the teachings of the present invention, a coating device for selectively applying a coating to surfaces of an object, the device applying the coating based upon optical properties of the surfaces such that the coating is applied to surfaces of a first type and is not applied to surfaces of a second type, the first type of surface being optically distinguishable from the second type of surface, the coating device comprising: a) a housing which includes an application compartment; b) at least one object-holding element deployed within the application compartment, the object-holding element configured to hold the object to which a coating is applied; c) a displaceable applicator base deployed within the application compartment, the applicator base including: i) at least one coating applicator aligned so as to deposit a fluid whereby at least a portion of the object is coated; and ii) at least one optical scanning device deployed so as to scan at least a portion of the object, the optical scanning device configured so as to produce output indicative of the different types of surfaces of the object, the displacement of the applicator base resulting in a variance of a spatial relationship between the coating applicator base and the object; d) at least one fluid delivery system in fluid communication so as to supply the fluid to the coating applicator; e) a processing unit being responsive at least to the output so as to selectively activate the coating applicator, thereby applying the coating substantially only to surfaces of the first type; and f) a drive system configured so as to provide relative motion between the surface of the object and the applicator base.

According to a further teaching of the present invention, the housing includes a base housing section and a detachable housing section.

According to a further teaching of the present invention, the application compartment is defined by portions of both the base housing and the detachable housing section.

According to a further teaching of the present invention, the base housing section includes the displaceable applicator base, at least a portion of the fluid delivery system, and the processing unit, and at least a first portion of the drive system, and the detachable housing section includes the object-holding element and at least a second portion of the drive system.

According to a fuirther teaching of the present invention, the base housing section includes at least one fluid delivery system.

According to a further teaching of the present invention, the detachable housing section is disposable.

According to a further teaching of the present invention, the drive system is configured so as to rotate the object-holding element about an axis perpendicular to a direction of application of the coating applicator.

According to a further teaching of the present invention, the at least one object-holding element is implemented as two object-holding elements configured so as to simultaneously support the object at two different regions along a length of the object.

According to a further teaching of the present invention, the two object-holding elements are mechanically linked so as to rotate synchronously about a single axis, the axis being perpendicular to a direction of application of the coating applicator.

According to a firther teaching of the present invention, the at least one coating applicator includes a pressure-pulse actuated drop-ejection system with at least one nozzle.

According to a further teaching of the present invention, the at least one fluid delivery system is deployed in the base housing.

According to a further teaching of the present invention, the at least one coating applicator is implemented as a plurality of coating applicators and the at least one fluid delivery system is implemented as a like number of fluid delivery systems, each fluid delivery system supplying a different fluid coating material to the coating applicator with which the each fluid delivery system is in fluid communication.

According to a further teaching of the present invention, the coating applicator, and the fluid delivery system are included in a removable sub-housing, the removable sub-housing being detachably connected to the displaceable applicator base.

According to a further teaching of the present invention, the spatial relationship is varied along two axes, a first axis that is parallel to a direction of application of the coating applicator, and a second axis that is perpendicular to the direction of application of the coating applicator.

According to a further teaching of the present invention, the object is a catheter that includes a balloon portion on which a stent is deployed, such that the stent is a surface of the first type and the balloon is a surface of the second type.

According to a firrther teaching of the present invention, the processing unit is responsive to an indication of the relative motion so as to change operational parameters of the coating device as required.

There is also provided according to the teachings of the present invention, a coating method for selectively applying a coating to surfaces of an object, the method applying the coating based upon optical properties of the surfaces such that the coating is applied to surfaces of a first type and is not applied to surfaces of a second type, the first type of surface being optically distinguishable from the second type of surface, the coating device comprising: generating relative movement between the object and at least one optical scanning device and at least one coating applicator; optically scanning at least a portion of the object by use of the at least one optical scanning device so as to produce output indicative of the different types of surfaces of the object; responding to the output by selectively activating the coating applicator, thereby applying the coating substantially only to surfaces of the first type.

According to a fuirther teaching of the present invention, the relative movement includes rotating the object about an axis perpendicular to a direction of application of the coating applicator.

According to a further teaching of the present invention, there is also provided simultaneously supporting the object at two different regions along a length of the object.

According to a further teaching of the present invention, the selective activation includes selectively activating a pressure-pulse actuated drop-ejection system with at least one nozzle.

According to a further teaching of the present invention, the selective activation includes selectively activating a pressure-pulse actuated drop-ejection system with at least one nozzle that is included in a removable sub-housing, the removable sub-housing further including a fluid delivery system in fluid communication so as to supply coating material to the coating applicator.

According to a further teaching of the present invention, the applying is preformed by selectively activating one of a plurality of coating applicators, wherein the at least one coating applicator implemented as the plurality of coating applicators, each of the plurality of coating applicators applying a different coating.

According to a further teaching of the present invention, the applying is preformed by selectively activating, in sequence, the plurality of coating applicators, thereby applying a plurality of layered coats, each one of the plurality of layered coats being of a coating material that is different from adjacent layered coats.

According to a further teaching of the present invention, responding to the output includes the output being indicative of a balloon portion of catheter and a stent deployed on the balloon, such that the stent is a surface of the first type and the balloon is a surface of the second type.

According to a further teaching of the present invention, responding to the output includes the output being indicative only of a surface of the first type thereby applying the coating to substantially the entire surface of the object.

According to a further teaching of the present invention, there is also provided varying a spatial relationship between the coating applicator and the object.

According to a further teaching of the present invention, the varying is along two axes, a first axis that is parallel to a direction of application of the coating applicator, and a second axis that is perpendicular to the direction of application of the coating applicator.

According to a further teaching of the present invention, the varying is accomplished by displacing the coating applicator.

According to a further teaching of the present invention, the varying is accomplished by varying the spatial relationship between the object and a displaceable applicator base upon which the at least one coating applicator and the at least one optical scanning device are deployed.

According to a further teaching of the present invention, controlling the varying is accomplished by the processing unit.

According to a further teaching of the present invention, there is also provided responding to an indication of the relative motion so as to change operational parameters of the coating device as required.

According to a further teaching of the present invention, generating relative movement, the optically scanning at least a portion of the object, and the selectively activating the coating are preformed within a housing.

BRIEF DESCRIPTION OF THE DRAWINGS

The invention is herein described, by way of example only, with reference to the accompanying drawings, wherein.

DESCRIPTION OF THE PREFERRED EMBODIMENTS

The present invention is a method and device, which is suitable for use in an operating theater just prior to implantation, for selectively applying a medical coating to an implantable medical device, for example a stent.

The principles and operation of a coating-device according to the present invention may be better understood with reference to the drawings and the accompanying description.

By way of introduction, the embodiment discussed herein is a device for applying a medical coating to a stent deployed on a catheter, the coating being applied just prior to implantation and if desired in the operating theater. The use of optical scanning devices enables a processing unit to distinguish between the surface area of the stent and the surface area of the catheter. The processing unit selectively activates the coating applicator so as to apply the coating to substantially only the stent and not the balloon or other portion of the catheter. The coating applicator discussed herein is, by non-limiting example, a pressure-pulse actuated drop-ejection system with at least one nozzle. A readily available pressure-pulse actuated drop-ejection system, which is well suited for the present invention, is a drop-on-demand inkjet system. It should be noted, however, that any coating application system that may be selectively activated is within the intentions of the present invention. While the discussion herein is specific to this embodiment, which is intended for use in an operating theater, among other places, this embodiment it is intended as a non-limiting example of the principals of the present invention. It will be readily apparent to one skilled in the art, the range of applications suited to the principals of the present invention. Even the device described herein, as a non-limiting example, with minor adaptations to the object-holding element and choice of fluid coating materials, is well suited for a wide range of objects to which a coating is applied.

Figure 1:
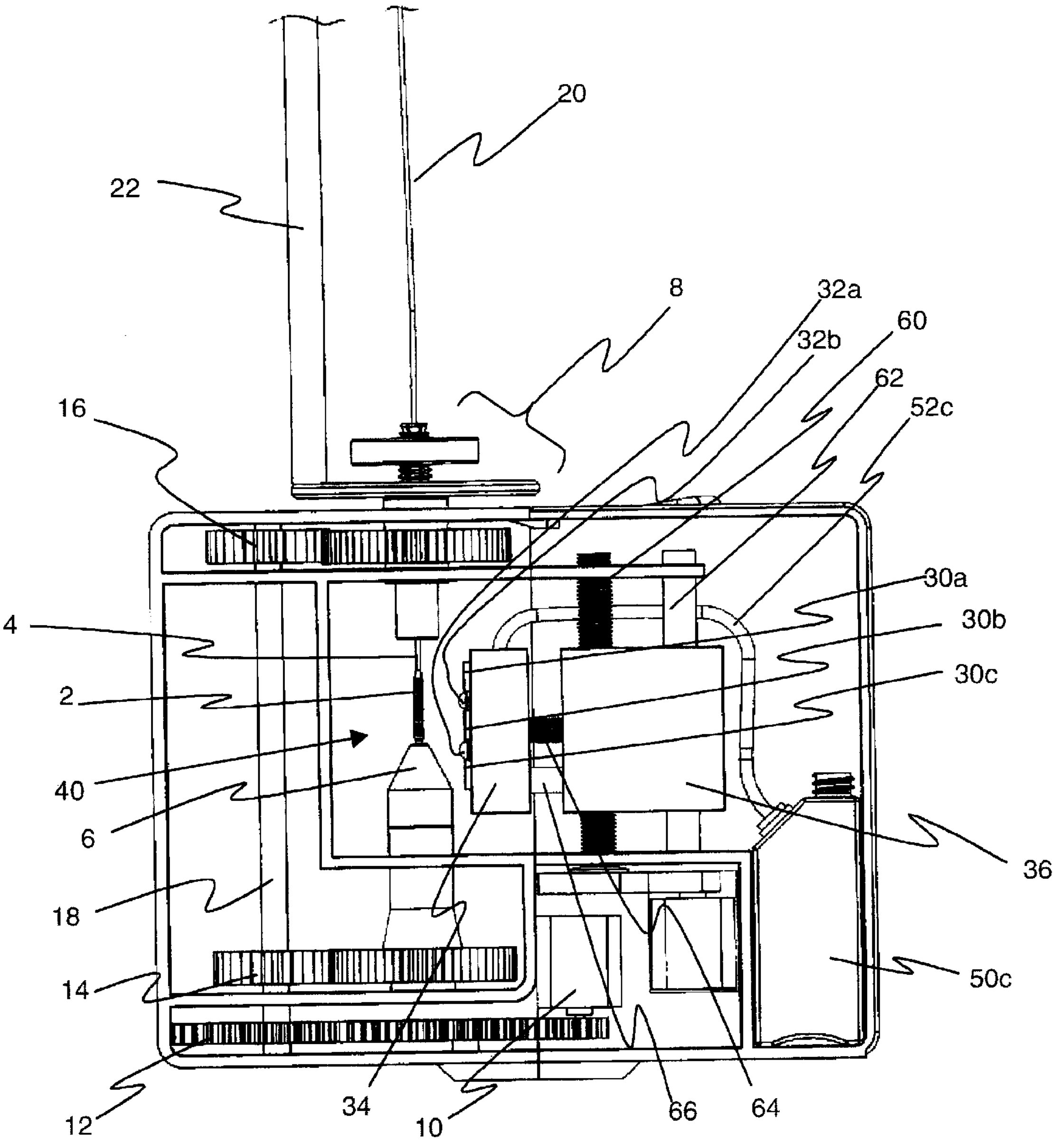
FIG. 1 is a cut-away side elevation of a stent coating device constructed and operative according to the teachings of the present invention.
Figure 2:
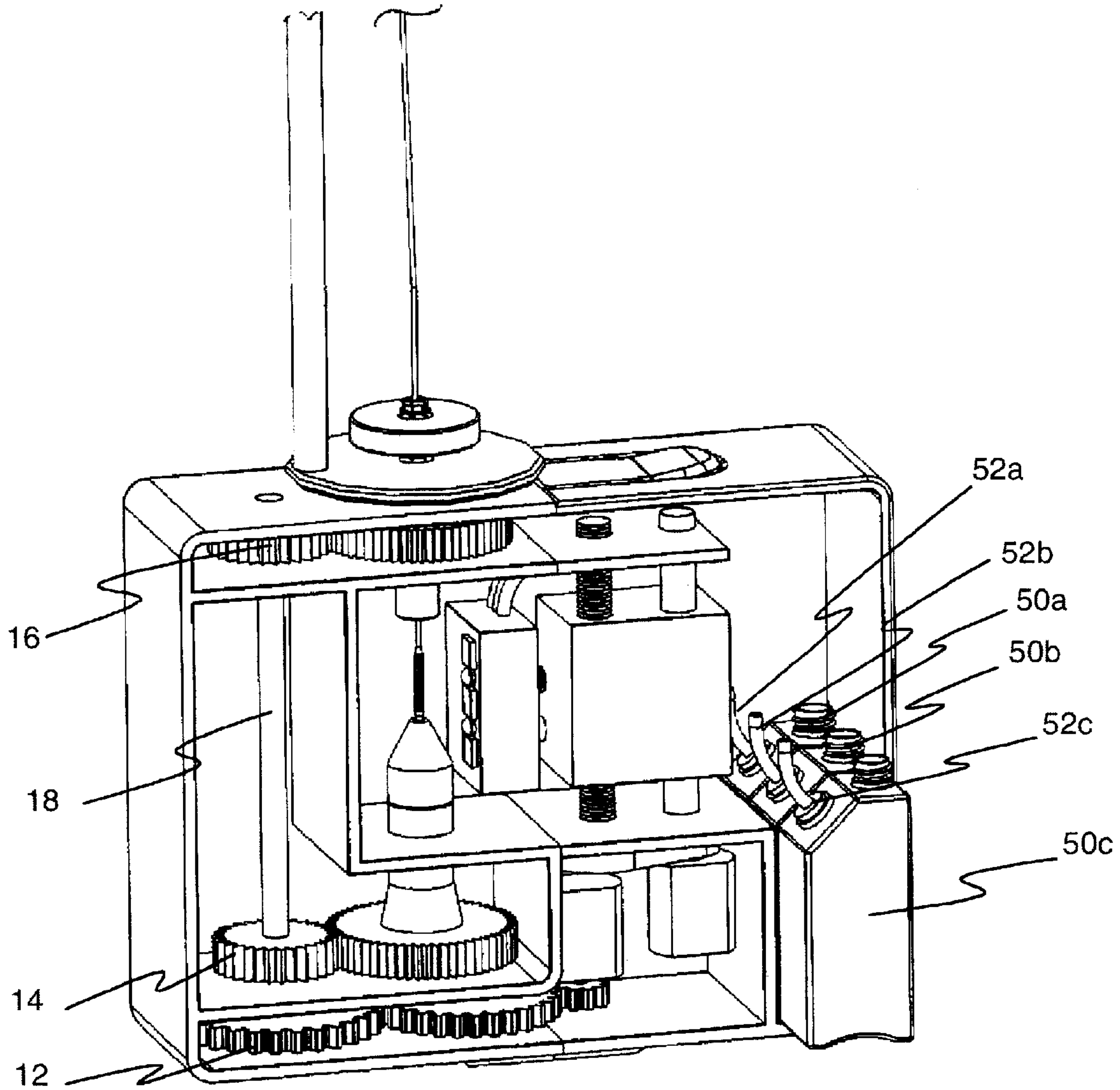
FIG. 2 is a cut-away perspective view of the stent coating device of FIG. 1.
Figure 6:
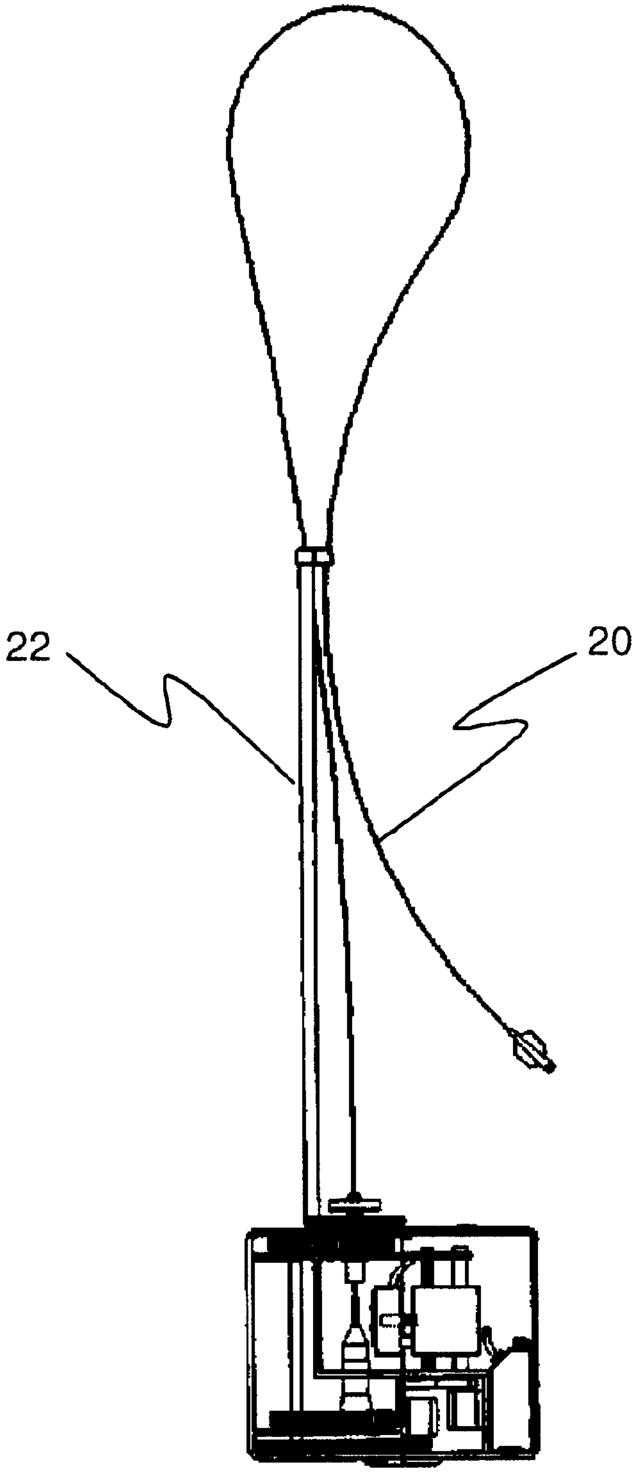
FIG. 6 is a side elevation of the stent coating device of FIG. 1 showing the full length of a catheter being supported by the support antenna.

Referring now to the drawings, as mentioned above, FIG. 1 illustrates a device for applying a coating to a stent 2 that is deployed on a catheter 4. The coating being applied may be a synthetic or biological, active or inactive agent. The perspective view of FIG. 2 is of the same side of the device as FIG. 1, and therefore when the description of elements of the device will be better understood, FIG. 2 will be referenced. The catheter 4 is placed in an application compartment 40 and held in position by a rotatable catheter-holding base 6 and a rotatable upper catheter-holding element 8, which are configured for substantially continued rotation, that is they may complete a plurality of full 360 degree rotations, as required, during the coating process. The actual rotation may be substantially fully continuous (non-stop) or intermittent. The upper catheter-holding element will be discussed in detail below with regard to FIG. 4. The enclosed application compartment provides a sterile environment in which the coating process is performed. The rotation of the catheter-holding base and the upper catheter-holding element is actuated and synchronized by a motor 10 and gear system that includes gear clusters 12, 14, 16, and shaft 18 (see also FIG. 2). Alternatively, the gears may be replaced by drive belts or drive chains. The remaining length of the catheter 20 is supported by a support antenna 22, as illustrated, by non-limiting example, in FIG. 6. As noted above, the object-holding elements may be modified so as to hold any object suitable for coating according to the teachings of the present invention.

The coating is applied by a drop-on-demand ink-jet system in association with an optical scanning device and processing unit. As the object is rotated by the object-holding element, the optical scanning device scans the surface of the object. The out-put from the scanning device is used by the processing unit to determine if the surface area currently aligned with the coating applicator is of the type of surface to be coated. When it is determined that the desired type of surface is aligned with the coating applicator, the processing unit activates the coating applicator and the coating is dispensed. The embodiment shown here includes three ink-jet coating applicators 30*a*, 30*b*, and 30*c*, and two optical scanning devices 32*a* and 32*b*. The optical scanning devices may be configured to generate digital output or an analog signal, which is in turn analyzed by the processing unit. It should be noted that the number of coating applicators and scanning devices may be varied to meet design or application requirements. The three coating applicators and the two optical scanning devices are mounted on a displaceable applicator head 34. The position of the applicator head within the application compartment, and thereby the spatial relationship between the coating applicator and the stent, or other object being coated, is regulated by the application control module 36, which is, in turn, controlled by the processing unit. The change of position of the applicator head is effected vertically by turning the vertical positioning screw 60 in conjunction with guide shaft 62, and the horizontally by turning the horizontal positioning screw 64 in conjunction with guide shaft 66. The vertical repositioning in conjunction with the rotation of the object enables the coating applicator to traverse substantially the entire surface of the object requiring coating.

Fluid coating material is stored in three fluid reservoirs 50*a*, 50*b*, and 50*c* (see FIG. 2), and supplied to the respective coating applicators by the fluid supply hoses 52*a*, 52*b* and 52*c* (see FIG. 2). In general use, each of the fluid reservoirs contains a different coating material, thus, each coating applicator will deposit a different coating material on the stent or other objected being coated, as required. Further, a plurality of coats may be applied, each coat being of a different coating material and, if required, of a different thickness. Thus, at the time of coating, a single appropriate coating material may be chosen from the materials provides, or a combination of coatings may be chosen. It should be noted that while the fluid reservoirs are shown here in a compartment inside the device housing, this need not always be the case, and the reservoirs may be external to the housing.

Figure 3:
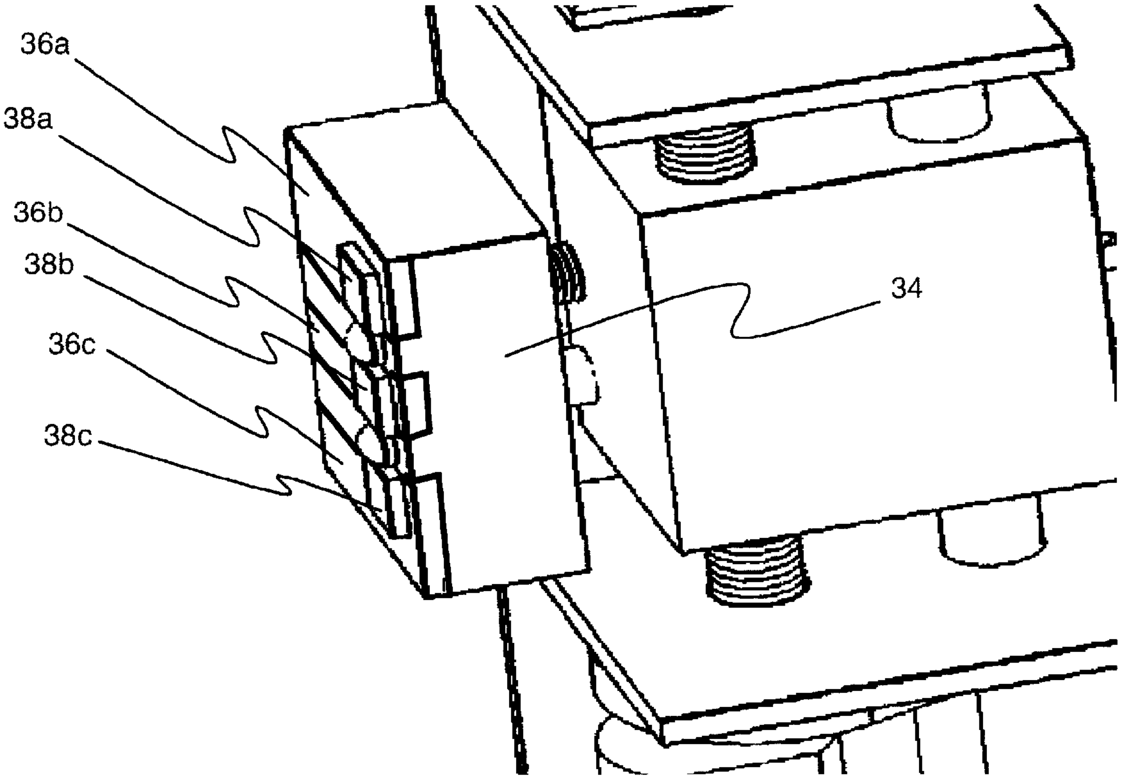
FIG. 3 is a perspective detail of an alternative displaceable applicator head constructed and operative according to the teachings of the present invention, shown here configure with disposable coating applicators.

It should be noted that, alternatively, the ink-jet system may be deployed in a disposable housing that also includes a fluid reservoir filled with coating material. The fluid reservoir may be an enclosed volume that is integral to the disposable housing or it may be a coating filled cartridge that is inserted into a receiving cavity in the disposable housing. In this case, as illustrated in FIG. 3, the displaceable applicator head 34 is configured so as to accept one or more of the disposable housings 36*a*, 36*b*, and 36*c*, which in turn house ink-jet coating applicators 38*a*, 38*b*, and 38*c* respectively. The fluid reservoirs (not shown) for each applicator are housed in that portion of the disposable housing that is deployed within the displaceable applicator head 34.

Figure 4:
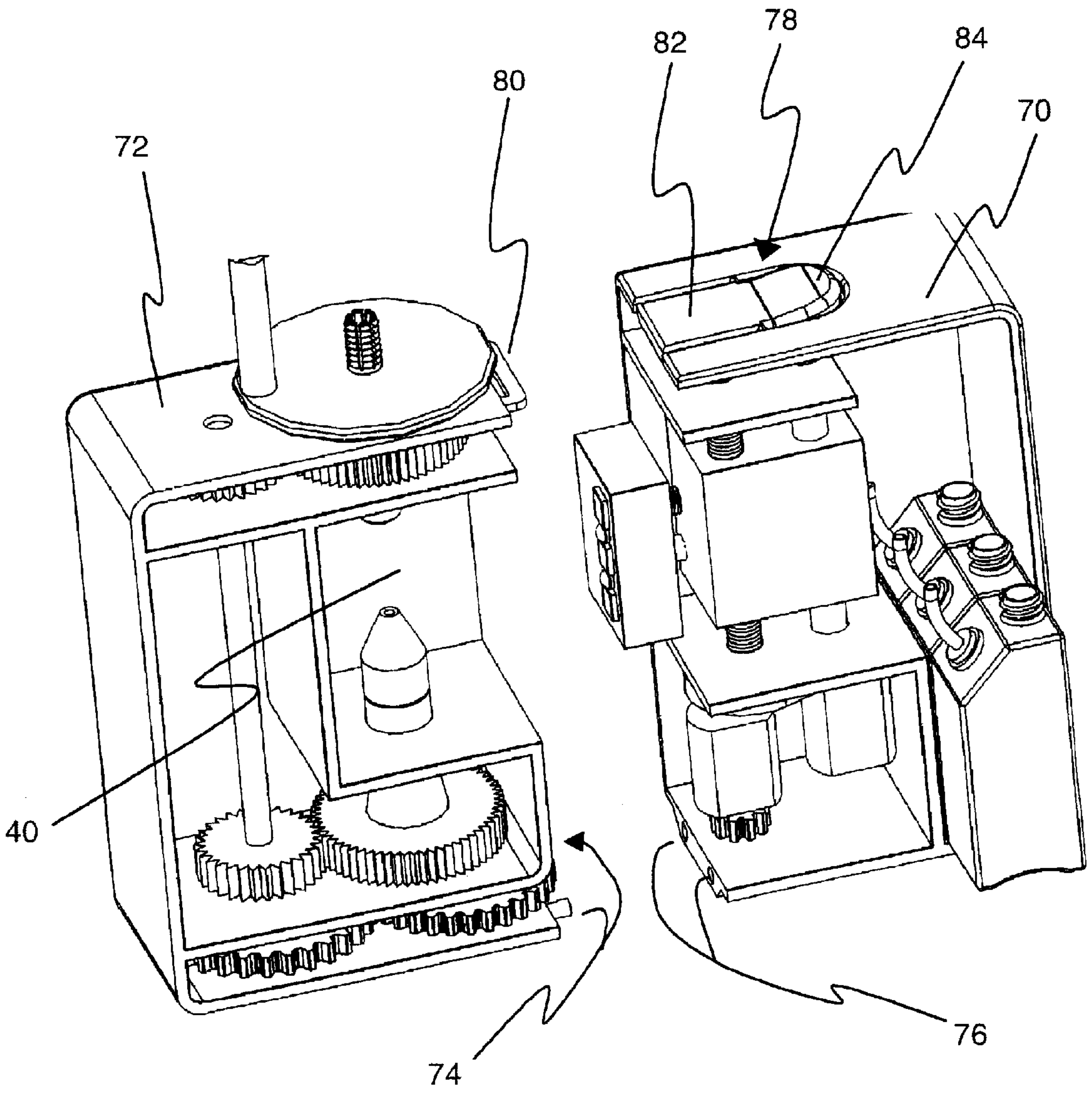
FIG. 4 is a cut-away perspective view of the stent coating device of FIG. 1, showing the detachable section of the housing separated from the base section of the housing.

FIG. 4 illustrates how the base housing section 70 and the detachable housing section 72 are interconnected. The two sections are held together by inserting pins 74, extending from the detachable housing section, into the corresponding holes 76, located in the base housing section, and engaging the latch mechanism 78 with the catch element 80. Detachment of the two sections is accomplished by pressing the release "button" 84, which raises the end 82 of the latch thereby releasing the catch element. The two sections are then pulled apart. As seen here more clearly, the application compartment is defined by a top, floor and three walls located in the detachable housing section and one wall on the base housing section. The detachable housing section is configured so as to be disposable, or if desired, easily cleaned and re-sterilized.

Figure 5:
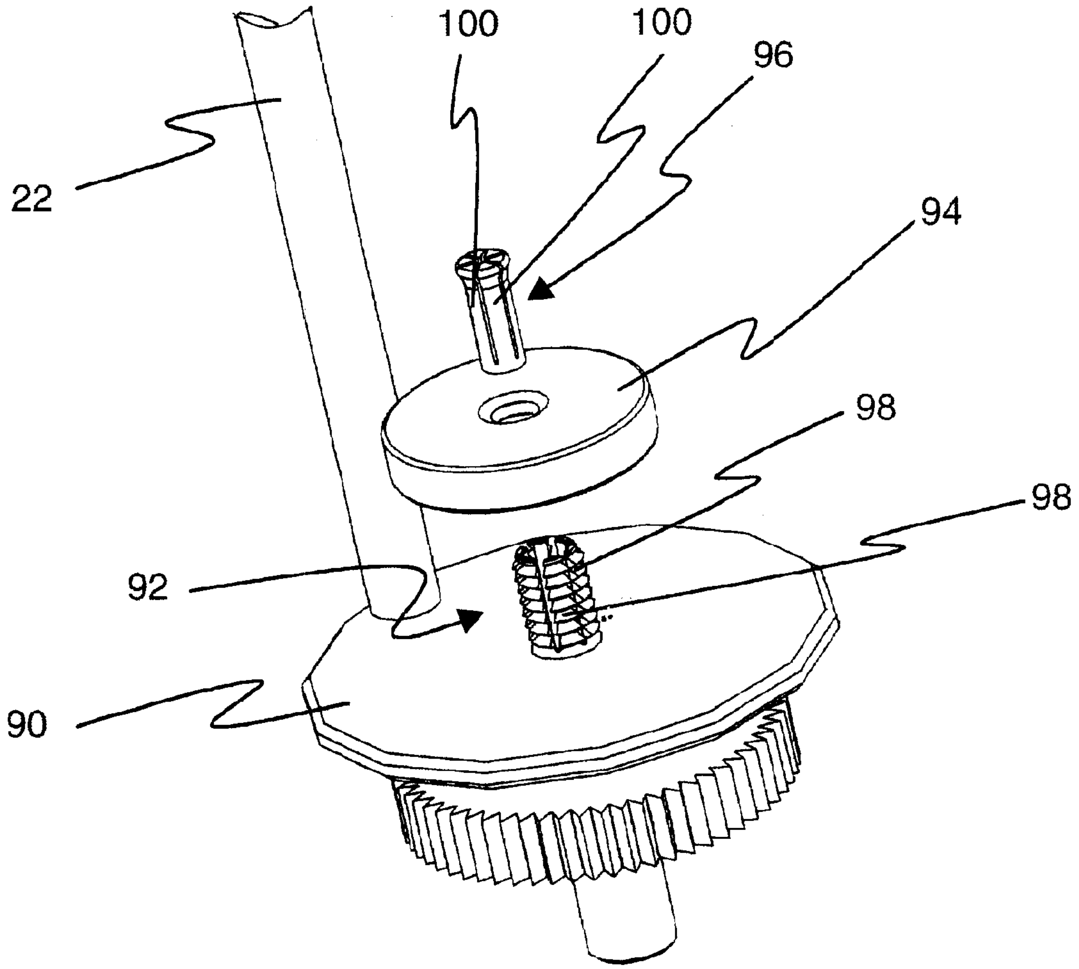
FIG. 5 is a perspective detail of an upper stent holding element, constructed and operative according to the teachings of the present invention.

The detail of FIG. 5 shows the components of the upper catheter-holding element. Extending from substantially the center of the rotating base plate 90, is a threaded tube 92. This tube is the external end of the passageway through which the catheter tip with the stent attached is inserted in order to deploy the stent in the application compartment of the coating device. The tube is cut longitudinally several times, to create threaded sections 98, here six, that are configured so as to flex outward from the center. The tightening-disk 94, has a correspondingly threaded center hole for deployment on the tube 92 such that when the tightening-disk is brought to a position proximal to the base plate, the threaded sections near the end of the tube will flex outwardly thereby enlarging the diameter of the opening. The gripping element 96 also has divergently flexing "fingers" 100. In operation, the gripping element is deployed around the catheter, which is then passed through the tube and into the application compartment. Once the catheter is positioned on the catheter-holding base, the gripping element is at least partially inserted into the opening of the tube. The tightening-disk 94 is then rotated about the tube, and thereby brought to a position proximal to the end of the tube, the outwardly flexing sections of the tube 98 are brought into an un-flexed state thereby decreasing the diameter of the opening. The decrease in the diameter of the tube opening pushes the "fingers" of the gripping element against the catheter, thereby holding the catheter in place.

A non-limiting example of the stent coating process as accomplished by the above describe device would be as follows:

1. The fluid reservoirs are filled with the required fluid coating materials.
2. The parameters of the coating are inputted into the processing unit. The parameters may include, by non-limiting example, the coating material to be applied, the thickness of the coating, number of multiple layers of different coating material, the order in which the layered materials are to be applied, and the thickness of each layer. The parameters may be determined by the physician at the time the coating is applied or the parameters may be pre-set, such as those determined by medical regulations. In the case of pre-set parameters, the physician would simply input a "start" command.
3. The catheter is positioned in the application compartment and the upper catheter-holding element is tightened.
4. As the catheter rotates, the optical scanning device scans the surface of the catheter, to distinguish between the surface of the balloon and the surface of the stent.
5. When a portion of the surface of the stent is detected and determined to be in alignment with the appropriate coating applicator, the processing unit selectively activates the applicator, thereby ejecting the necessary amount of coating material, which is deposited substantially only on the surface of the stent.
6. Throughout the coating process, the position of the applicator head is adjusted as required. This adjustment may bring the coating applicator closer to, or farther away from, the surface of the stent, and it may adjust the vertical deployment of the coating applicator, thereby allowing different areas of the surface of the stent to be coated. Further, if a different fluid coating material is needed for a different layer of the coating, the coating applicator for that particular coating material may be brought into appropriate alignment for deposition of the new coating material on the stent.
7. When the coating process is completed, the catheter with the now coated stent is removed from the device, and the stent is ready for implantation.
8. The detachable housing section is removed and may be cleaned and sterilized for re-use, or simply discarded.

It should be noted that in some cases it may be desirable to coat substantially the entire surface of the object being coated. This may be accomplish in at least two ways. The object itself may have only one type of surface. Alternatively, the scanning device may be configured so as to provide adjustable scanning sensitivity. In such a case, the sensitivity of the scanning device may be adjusted such that the out-put is indicative of only one type of surface and the processing unit is unable to distinguish between different types of surfaces.

It will be appreciated that the above descriptions are intended only to serve as examples, and that many other embodiments are possible within the spirit and the scope of the present invention.

What is claimed is:

1. A coating method for selectively applying a coating to surfaces of a stent, the method applying the coating based upon optical properties of the surfaces such that the coating is applied to surfaces of the stent and is not applied to surfaces of a balloon portion of a catheter on which the stent is mounted, the surfaces of the stent being optically distinguishable from the surfaces of the balloon portion of the catheter, the coating method comprising:

(a) generating relative movement between the stent and at least one optical scanning device and at least one coating applicator;

(b) optically scanning at least a portion of the stent by use of said at least one optical scanning device so as to produce output indicative of the different types of surfaces of the stent and balloon portion of the catheter;

(c) responding to said output by selectively activating said coating applicator, thereby applying the coating substantially only to surfaces of the stent.

2. The coating method of claim 1, wherein said relative movement includes rotating the object about an axis perpendicular to a direction of application of said coating applicator.

3. The coating method of claim 1, further comprising simultaneously supporting the object at two different regions along a length of the object.

4. The coating method of claim 1, wherein said selective activation includes selectively activating a pressure-pulse actuated drop-ejection system with at least one nozzle.

5. The coating method of claim 1, wherein said selective activation includes selectively activating a pressure-pulse actuated drop-ejection system with at least one nozzle that is included in a removable sub-housing, said removable sub-housing further including a fluid delivery system in fluid communication so as to supply coating material to said coating applicator.

6. The coating method of claim 1, wherein said applying is performed by selectively activating one of a plurality of coating applicators, wherein said at least one coating applicator implemented as said plurality of coating applicators, each of said plurality of coating applicators applying a different coating.

7. The coating method of claim 6, wherein said applying is performed by selectively activating, in sequence, said plurality of coating applicators, thereby applying a plurality of layered coats, each one of said plurality of layered coats being of a coating material that is different from adjacent layered coats.

8. The coating method of claim 1, wherein responding to said output includes said output being indicative only of a surface of the first type thereby applying the coating to substantially the entire surface of the object.

9. The coating method of claim 1, further comprising varying a spatial relationship between said coating applicator and the object.

10. The coating method of claim 9, wherein said varying is along two axes, a first axis that is parallel to a direction of application of said coating applicator, and a second axis that is perpendicular to said direction of application of said coating applicator.

11. The coating method of claim 10, wherein said varying is accomplished by displacing said coating applicator.

12. The coating method of claim 11, wherein said varying is accomplished by varying the spatial relationship between said object and a displaceable applicator base upon which said at least one coating applicator and said at least one optical scanning device are deployed.

13. The coating method of claim 12, wherein controlling said varying is accomplished by said processing unit.

14. The coating method of claim 1, further comprising responding to an indication of said relative motion so as to change operational parameters of the coating device as required.

15. The coating method of claim 1, wherein generating relative movement, said optically scanning at least a portion of the object, and said selectively activating said coating are preformed within a housing.

* * * * *